(12) United States Patent
Miner

(10) Patent No.: US 7,722,577 B2
(45) Date of Patent: May 25, 2010

(54) BUBBLE FREE—SELF PRIMED IV SET

(75) Inventor: Tom M. Miner, Alpine, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 988 days.

(21) Appl. No.: 11/205,236

(22) Filed: Aug. 16, 2005

(65) Prior Publication Data

US 2006/0189937 A1    Aug. 24, 2006

Related U.S. Application Data

(60) Provisional application No. 60/654,705, filed on Feb. 18, 2005.

(51) Int. Cl.
*A61M 5/14* (2006.01)

(52) U.S. Cl. ...................................... 604/251

(58) Field of Classification Search ................. 604/246, 604/251–255
See application file for complete search history.

(56) References Cited

U.S. PATENT DOCUMENTS

| | | | | |
|---|---|---|---|---|
| 3,390,677 | A | * | 7/1968 | Razimbaud ................. 604/414 |
| 3,631,654 | A | * | 1/1972 | Riely et al. ....................... 96/6 |
| 4,013,072 | A | | 3/1977 | Jess |
| 4,200,095 | A | | 4/1980 | Reti |
| 5,308,314 | A | * | 5/1994 | Fukui et al. ................. 604/6.11 |
| 5,489,385 | A | | 2/1996 | Raabe et al. |
| 5,779,674 | A | | 7/1998 | Ford |
| 6,099,512 | A | * | 8/2000 | Urrutia ........................ 604/251 |
| 2002/0156431 | A1 | * | 10/2002 | Feith et al. ................... 604/247 |
| 2005/0171491 | A1 | * | 8/2005 | Minh Miner et al. ......... 604/257 |

OTHER PUBLICATIONS

Braun, Product Detail, http://www.bbraunoem-industrial.com/products/details.cfm?prodid=B0843225&id-Caps&area=C, p. 1, Apr. 12, 2005.

* cited by examiner

*Primary Examiner*—Kevin C Sirmons
*Assistant Examiner*—Bradley J Osinski
(74) *Attorney, Agent, or Firm*—Mony R. Ghose; Craig Metcalf; Kirton & McConkie

(57) ABSTRACT

A bubble free, self-priming IV set for use in the administration of liquids that includes a drip chamber comprising a chamber inlet and a chamber outlet, a bubble isolation device disposed within the drip chamber that prevents air bubbles from exiting the chamber outlet, a tube having an inlet end coupled to the chamber outlet of the drip chamber and an outlet end, and an end plug that includes an air vent. The end plug may be coupled to the outlet end of the tube and is a flow restrictor so that when a liquid is moving through the tube, the velocity of the liquid flow is controlled such that the front of the liquid does not trap bubbles in the tube.

25 Claims, 5 Drawing Sheets

BUBBLE FREE—SELF PRIMED IV SET

CROSS-REFERENCED RELATED APPLICATIONS

This application claims the benefit of U.S. Provisional Application No. 60/654,705, filed Feb. 18, 2005.

BACKGROUND OF THE INVENTION

This invention relates generally to tubing sets used in the administration of liquids to a patient that are commonly referred to as intravascular ("IV") sets and more particularly concerns bubble free, self-priming IV sets. An IV set according to the invention is used broadly herein to describe tubing sets used in the arterial, intravenous, intravascular, peritoneal, and non-vascular administration of fluid. Of course, one of skill in the art may use IV set to administer fluids to other locations than those listed within a patient's body.

One common method of administering fluids into a patient's blood flow is through an IV set. An IV set is an apparatus that generally includes a connector for connection to a fluid reservoir, a drip chamber used to determine the flow rate of fluid from the fluid reservoir, tubing for providing a connection between the fluid reservoir and the patient, and a connector for attachment to a catheter that may be positioned intravenously in a patient. An IV set may also include a Y-connector that allows for the piggybacking of IV sets and for the administration of medicine from a syringe into the tubing of the IV set.

It is a generally good practice to remove air from IV sets which access a patient's blood flow. While this concern is critical when accessing arterial blood, it is also a concern when accessing the venous side. Specifically, if air bubbles are allowed to enter a patient's blood stream while receiving the intravenous administration of liquids, the air bubbles can form an air embolism and cause serious injury to a patient.

Normally, in a majority of adults, the right atrium and the left atrium are completely separated from each other so that the blood and air bubbles are moved from the right atrium, to the right ventricle, and then to the lungs where the air bubbles may be safely vented. The bubble free blood is then returned to the left atrium, where the blood is moved to the left ventricle and then sent throughout the body.

However, in infants and in a small portion of the adult population, the right atrium and left atrium are not completely separated. Consequently, air bubbles can move directly from the right atrium into the left atrium and then be dispersed throughout the body. As a result, these air bubbles may cause strokes, tissue damage, and/or death. Therefore, it is important to prevent air bubbles from entering a patient's blood stream.

In spite of the importance of removing air bubbles while priming an IV set for use in the intravenous administration of liquids, the complete removal of air bubbles can be a time consuming process. The process may also lead to contamination of the IV set by inadvertently touching a sterile end of the IV set. Typically, when an IV set is primed, a clamp is closed to prevent liquid from moving from a drip chamber through the tubing. The IV set is then attached to an IV bag or bottle. Once attached, the drip chamber, which is typically made of a clear flexible plastic, may be squeezed to draw the liquid out of the IV bag or bottle and into the drip chamber. The drip chamber is allowed to fill about ⅓ to ½ full when the clamp is opened to allow liquid to flow through the tube to an end of the IV set.

This initial process, however, typically traps air in tubing which must be removed. For example, the flow of the liquid through the tubing of the IV set may be turbulent and can entrap air within the tube as the boundary layer between the liquid and the tubing is sheared. The flow rate out of the drip chamber may be higher than the flow rate of liquid entering the drip chamber. This can cause a bubble ladder to form as air is sucked from the drip chamber into the tubing.

Additionally, air bubbles may be generated as drops of liquid strike the surface of the pool of liquid within the drip chamber. These air bubbles can be pulled into the tubing of the IV set from the drip chamber. This problem may be aggravated in pediatric applications where the drip orifice may be smaller which may result in increased turbulence.

To remove air bubbles from the IV set, liquid from the IV bag or bottle is allowed to flow through the tubing while an attendant taps the tubing to encourage the air bubbles out the end of the IV set. As the liquid is allowed to flow out of the IV set to clear air bubbles from the tubing, the liquid is generally allowed to flow into a waste basket or other receptacle. During this procedure the end of the tubing may contact the waste basket or be touched by the attendant and thus, become contaminated. An additional shortcoming of this debubbling process is that it requires attention and time that could have been used to perform other tasks that may be valuable to the patient.

Another debubbling method is to directly remove air bubbles from the IV set. More specifically, if the IV set includes a Y-connector, air bubbles may be removed at the Y-connector by a syringe.

In some cases, a small pore filter may be used in the drip chamber to prevent air from entering the IV tubing from the drip chamber. However, the bubbles formed from the dripping action may become trapped on the filter, thus, reducing the flow of liquid through the filter to the IV tubing. However, the filter is normally positioned so that air may be trapped between the bottom of the filter and the bottom of the drip chamber.

Accordingly, a need exists for an IV set that is self-priming and bubble free, and which does not require constant attention and supervision. Additionally, a need exists for an IV set that prevents bubbles from entering the tubing during use, while providing flow rates that satisfy the needs of the patient.

BRIEF SUMMARY OF THE INVENTION

The apparatus of the present invention has been developed in response to the present state of the art, and in particular, in response to the problems and needs in the art that have not been fully solved by currently available IV sets. Thus, the present invention provides an IV set for use in intravenous administration of liquids that prevents air from being passed to a patient during the intravenous administration of liquids.

In accordance with the invention as embodied and broadly described herein in the preferred embodiment, an IV set is provided. According to one embodiment, the IV set may include a drip chamber having a chamber inlet and a chamber outlet and a bubble isolation device disposed within the drip chamber that prevents air bubbles from exiting the chamber outlet. Typically, IV sets are gravity fed so that the chamber inlet is disposed in a top surface and the chamber outlet is disposed in a bottom surface of the drip chamber. The IV set may also include a tube having an inlet end and an outlet end, with the inlet end of the tube coupled to the chamber outlet of the drip chamber.

Additionally, the IV set may include a means for venting air out of the tube, such as an end plug that has an air vent coupled to the outlet end of the tube. The air vent may include a hydrophobic material, which allows air to exit the IV set while preventing liquid from exiting. The air vent may also include several small holes which allow air to pass while limiting the passage of water through the end plug. The end plug and the air vent acts as a flow restrictor to the exiting air, so that when a liquid is moving through the tube, the velocity of the liquid flow is controlled such that the flow is generally laminar. The laminar flow of the liquid through the tube prevents air from becoming entrapped within the tube during priming and helps to completely eliminate the air from the tube during priming.

The bubble isolation device is a means for means for preventing bubbles from exiting the chamber outlet and may include an active portion that comprises a hydrophilic filter or an absorbent structure, such as a sponge. The bubble isolation device may also include an absorbent structure that includes a woven material and/or a mat of material. The mat may be sintered or adhered together by an adhesive. Additionally, the bubble isolation device may include a concave surface that is disposed within the drip chamber so that the liquid entering the drip chamber through the chamber inlet is directed toward the concave surface.

Where the active portion of the bubble isolation device includes a hydrophilic filter or an absorbent structure, the bubble isolation device may be shaped to match the profile and abuts the bottom surface of the drip chamber so that the active portion completely covers the chamber outlet. By disposing the bubble isolation device against the bottom surface of the drip chamber, air is prevented from being trapped between the bubble isolation device and the bottom surface of the drip chamber.

Where the bubble isolation device includes a concave surface, the bubble isolation device may be disposed to partition the chamber into a bubble isolation chamber and a calm fluid chamber. The bubble isolation chamber is above the concave surface and the calm fluid chamber is positioned below the concave surface but above the bottom surface of the drip chamber. The concave surface directs bubbles toward the surface of the liquid to be expelled as new bubbles are formed by the droplets of liquid striking the surface of the liquid.

The IV set may also include a particulate filter to prevent solid material from exiting the tube. Additionally, the IV set may include a zero dead space access port disposed between the inlet end and the outlet end of the tube. A zero dead space access port is designed to prevent the entrapment of air within the access port as liquid flows through the access port.

A method for priming the IV set described above may include the steps of coupling the chamber inlet to a source of the liquid, wetting the bubble isolation device with liquid, and using the bubble isolation device to prevent air bubbles from reaching the chamber outlet. Additionally, the method may include the steps of opening the clamp to permit liquid to flow through the tube, using the end plug to restrict the venting of air from the tube as liquid flows through the tube so that the fluid flow through the tube is laminar, and using the end plug to prevent liquid from exiting the outlet end of the tube.

As the configuration of the IV set varies, the method may also include additional steps. For example, where the bubble isolation device is an absorbent structure, the method may further include absorbing the liquid in the absorbent structure so that liquid does not pass the chamber outlet until the absorbent structure is saturated. Where the IV set includes a particulate filter, the method may include using the particulate filter to prevent material from the bubble isolation device from exiting the tube. Alternatively, where the tube includes a zero dead space access port, the method may include expelling all air from the zero dead space access port with the front of the liquid flowing through the tube.

Where the configuration of the IV set includes an end plug, the method may include the step of using the end plug to restrict the venting of air from the tube as liquid flows through the tube so that the volume of fluid flowing through the chamber inlet is greater than or about equal to the liquid flow through the chamber outlet. Alternatively, where the bubble isolation device includes a concave surface, the method may further include the steps of using the bubble isolation device to partition the chamber into a bubble isolation chamber and a calm fluid chamber and using the concave surface to retain the air bubbles in the bubble isolation chamber.

These and other features and advantages of the present invention will become more fully apparent from the following description and appended claims, or may be learned by the practice of the invention as set forth hereinafter.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the bubble free, self-priming IV set of the present invention, as represented in FIGS. 1 through 5, is not intended to limit the scope of the invention, as claimed, but is merely representative of presently preferred embodiments of the invention.

For this application, the phrases "connected to," "coupled to," and "in communication with" refer to any form of interaction between two or more entities, including mechanical, electrical, magnetic, electromagnetic, and thermal interaction. The phrase "attached to" refers to a form of mechanical coupling that restricts relative translation or rotation between the attached objects.

The phrase "attached directly to" refers to a form of attachment by which the attached items are either in direct contact, or are only separated by a single fastener, adhesive, or other attachment mechanism. The term "abutting" refers to items that are in direct physical contact with each other, although the items may not be attached together. The terms "integrally formed" refer to a body that is manufactured integrally, i.e., as a single piece, without requiring the assembly of multiple pieces. Multiple parts may be integrally formed with each other if they are formed from a single work piece.

Figure 1:
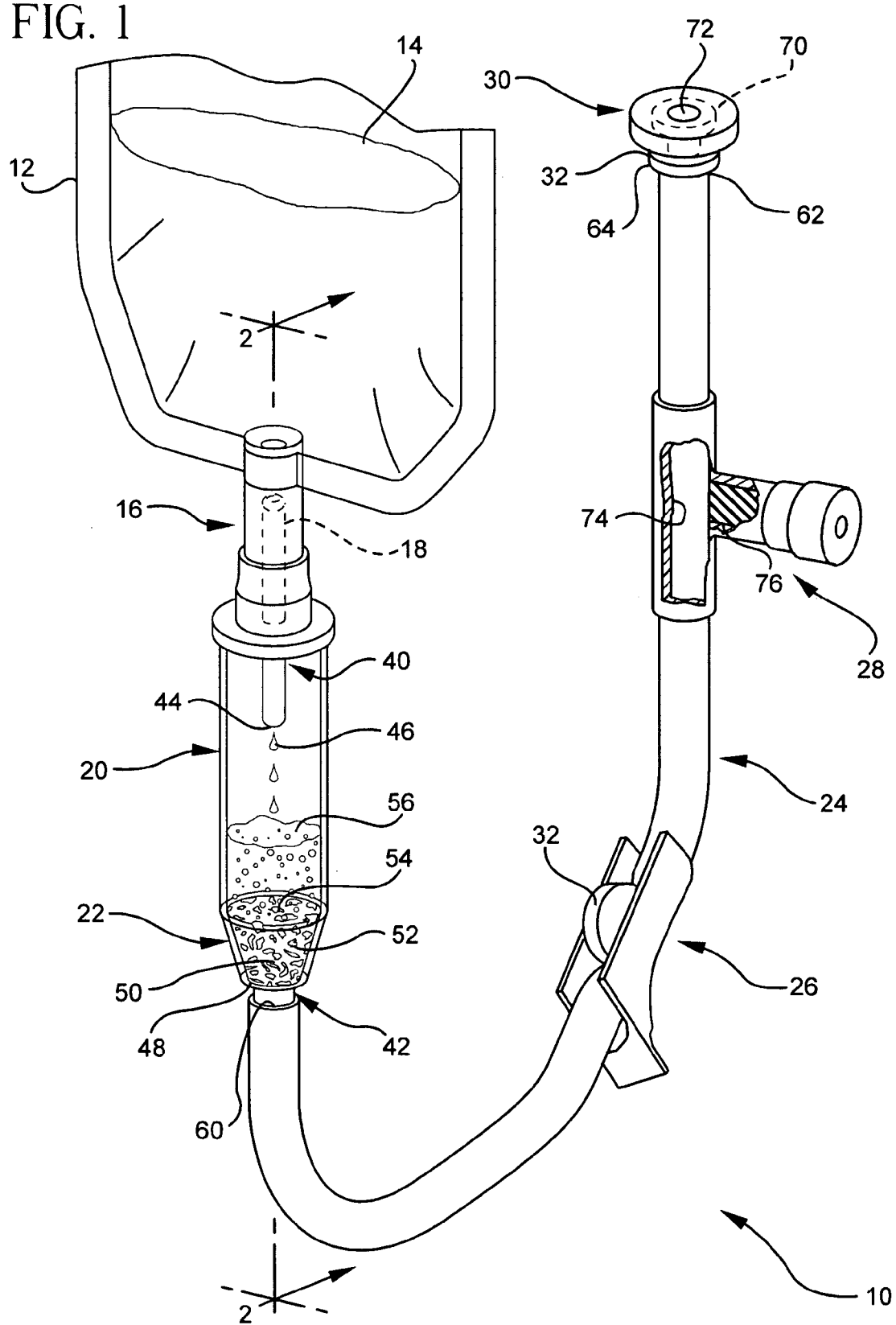
FIG. 1 is a perspective view of an IV set coupled to an IV bag.

FIG. 1 is a perspective view illustrating a bubble free, self-priming IV set 10 according to the invention. As shown, the IV set 10 may be connected to an IV bag 12, which provides a source of liquid 14 for priming the IV set 10. The IV set 10 may include a connector 16 for connection to the source of liquid 14, which may include a spike 18 or another type of connection known by those of skill in the art.

The IV set 10 may also include a drip chamber 20 that contains a bubble isolation device 22. The drip chamber 20 is a metering device that permits the flow rate of liquid 14 entering the IV set 10 to be determined. As the liquid 14 enters the drip chamber, air may be trapped within the liquid 14 to form air bubbles. The bubble isolation device 22 within the drip chamber 20 helps to prevent air bubbles from exiting the drip chamber 20 with the liquid 14.

The drip chamber 20 is connected to a tube 24. The tube 24 is a conduit used to convey fluid 14 from the drip chamber 20 and the IV bag 12 to a patient.

A clamp 26, a zero dead space access port 28, and an end plug 30 may be attached to the tube 24. The clamp 26 permits the flow of liquid 14 exiting the drip chamber 20 to be controlled and stopped. The zero dead space access port 28 permits another IV set (not shown) to be piggybacked onto the IV set 10 or to have medication directly added to the fluid 14 by a syringe (not shown). The zero dead space access port 28 is also designed not to trap air as the liquid 14 flows through it. The end plug 30 helps to protect an end 32 of the IV set from contamination and also helps to prevent air bubbles from moving through the tube 24 with the liquid 14.

Before the IV set 10 is attached to a source of liquid 14, the clamp 26 is typically closed to prevent the flow of fluid through the tube 24. As shown, the clamp 26 is a roller clamp 32. Once the IV set 10 is attached to a source of liquid 14, a vacuum may be formed by squeezing the drip chamber 20 to draw the liquid 14 from the IV bag 12 into the drip chamber 20.

The drip chamber 20 includes a chamber inlet 40 and a chamber outlet 42. The chamber inlet 40 is coupled to the connector 16 and as shown, the chamber inlet 40 is a tube 24 shaped to encourage the liquid 14 entering the drip chamber 20 to form droplets 46. As the liquid 14 initially enters the drop chamber 20 and forms droplets 46, the first of the droplets 46 fall toward the bottom surface 48 of the drip chamber 20 and wet the bubble isolation device 22.

The bubble isolation device 22 may have an active portion 50, which in this configuration of the invention is a sponge 52. The sponge 52 is an absorbent structure 54 that absorbs the liquid 14 and prevents the liquid 14 from passing through the chamber outlet 24 until the sponge 52 is saturated. The bubble isolation device 22 conforms to the profile of the bottom surface 48 and abuts the bottom surface 48 of the drip chamber 20 so that the active portion 50 of the bubble isolation device 22 fully covers the chamber outlet 42. As the sponge 52 is saturated with liquid 14, the liquid 14 displaces the air contained within the sponge 52. Because the sponge 52 conforms to the profile of the bottom surface 48 and fully covers the chamber outlet 42, air is not trapped between the bubble isolation device 22 and the chamber outlet 42.

Once the sponge 52 is saturated, the liquid 14 begins to pass through the chamber outlet 42 into the tube 24. Additionally, a pool 56 of the liquid 14 forms above the bubble isolation device 22. The bubble isolation device 22 also acts to slow the flow rate of fluid 14 from the drip chamber 20 into the tube 24.

The tube 24 includes an inlet end 60 coupled to the chamber outlet 42 and an outlet end 62. The outlet end 62 may include a fitting 64 for attachment to the end plug 30. The fitting 64 may be a luer type attachment that the end plug 30 protects from contamination.

Once the liquid 14 has filled the drip chamber 20 about ⅓ to about ½ full, the clamp 26 is opened to allow the liquid 14 to pass through the tube 24. As the liquid 14 moves through the tube 24, the air occupying the tube 24 is expelled through the end plug 30. The end plug 30 includes a vent 70 that may include a hydrophobic material and/or small pores that permits the air to pass but prevents the liquid 14 from passing through the vent 70. Thus, the end plug 30 prevents spillage of the fluid 14. The vent 70 may have a pore size that effectively retards the flow of air out of the tube 24.

The end plug 30 also includes an exit orifice 72 that may be sized to restrict the flow of air out of the exit orifice 72. The vent 70 may also restrict the flow of air out of the exit orifice 72.

Separately or in combination, the vent 70 and the exit orifice 72 allow the end plug 30 to act as a flow restrictor so that when the liquid 14 is moving through the tube 24, the remaining air in the tube 24 develops a back pressure that reduces the flow rate of the liquid 14 such that the flow is generally laminar. By controlling the velocity of the liquid 14 so that the flow is generally laminar, the liquid 14 is prevented from entrapping air in the tube 24 as the liquid 14 moves through the tube 24. If the liquid 14 is allowed to turbulently flow through the tube 24, air may become entrapped as the liquid 14 shears at the boundary layer and the front of the flow moves past air in the tube 24.

Because the end plug 30 is a flow restrictor, the end plug 30 also helps to maintain the flow rate of the liquid 14 exiting the drip chamber 20 to be less than or equal to the flow rate of liquid 14 entering the drip chamber 20. Should the flow rate of the liquid 14 exiting the drip chamber 20 be greater than the flow rate of liquid 14 entering the drip chamber 20, air may be pulled through the bubble isolation device 22 into the tube 24.

As the liquid 14 flows toward the end plug 30, the liquid 14 passes through the zero dead space access port 28. The zero dead space access port 28 is shaped to prevent liquid 14 from slowing or stagnating as it flows through the zero dead space access port 28 and to prevent air from becoming entrapped as the liquid 14 passes through the zero dead space access port 28. Thus, the zero dead space access port 28 may have a passage 74 that follows the internal shape of the tube 24 with a septum 76 shaping part of the passage 74.

The zero dead space access port 28 may be used to piggyback a second IV set (not shown). Alternatively, the zero dead space access port 28 may be used to administer medication into the tube 24 by a needle and syringe (not shown). For example, a sedative may be given to a patient through the zero dead space access port 28 rather than being directly injected into a patient, which may result in tissue damage at the injection site.

Once the liquid 14 reaches the end plug 30, the IV set 10 is bubble free, primed, and ready for use with a patient. For attachment to a patient, the end plug 30 is removed and the fitting 64 of outlet end 62 of the tube 24 may be attached to a needle (not shown), a catheter (not shown), another IV set (not shown), or another device known in the art.

Figure 2:
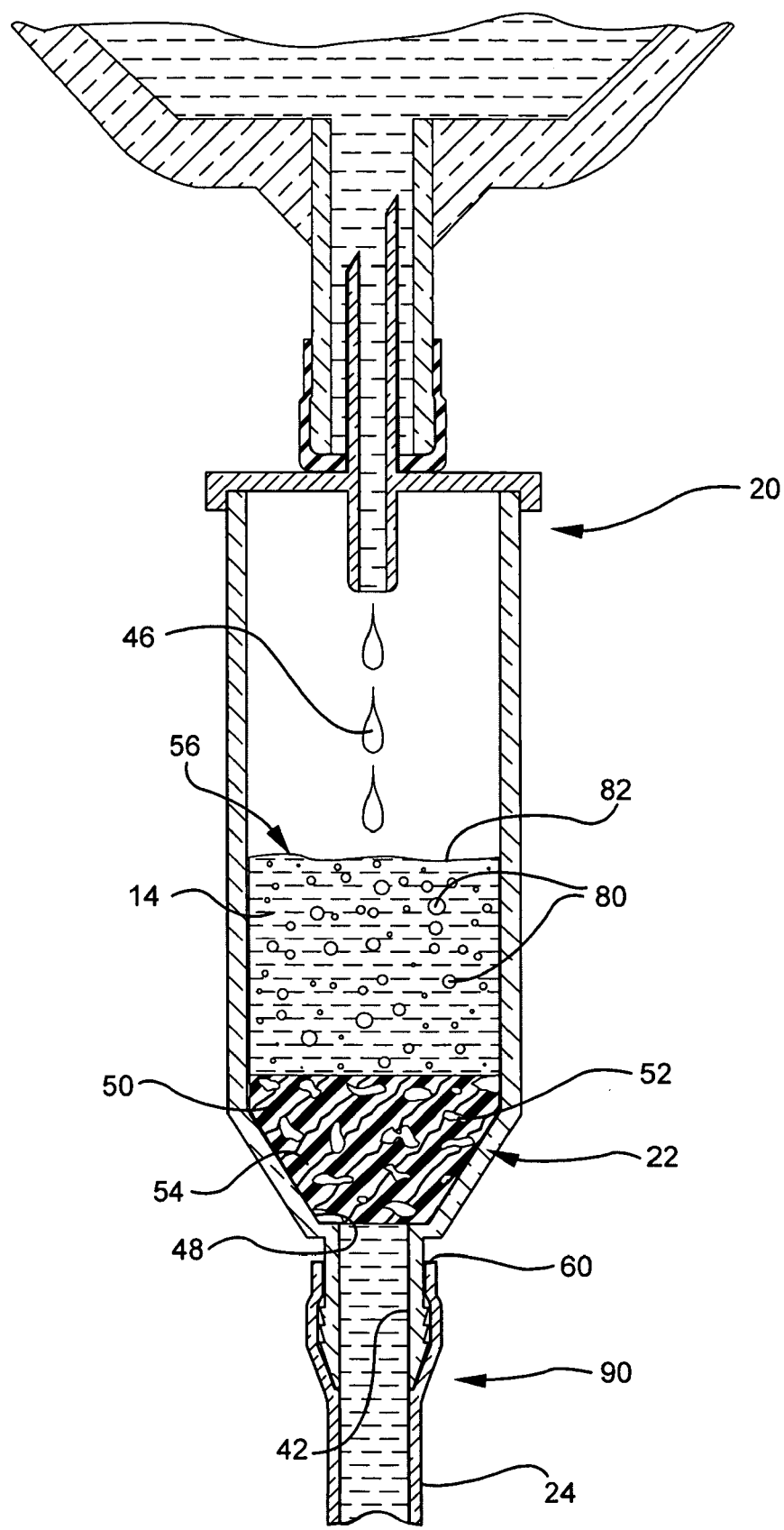
FIG. 2 is cross sectional view along line 2-2 of the bubble isolation device and the drip chamber of FIG. 1.

Referring to FIG. 2, a cross sectional view along line 2-2 illustrates the bubble isolation device 22 and the drip chamber 20 of FIG. 1. As shown, the bubble isolation device 22 conforms to the shape of the bottom surface 48 of the drip chamber 20 and completely covers the chamber outlet 42 with the active portion 50 of the bubble isolation device 22. By positioning the active portion 50 to completely cover the chamber outlet 42, air is prevented from being trapped under a frame (not shown) or between the bubble isolation device 22 and the bottom surface 48 as the fluid 14 moves through the bubble isolation device 22. In an alternative embodiment, the bubble isolation device 22 may include a frame (not shown) which is not part of the active portion 50 that supports the sponge 52. Additionally, the inlet end 60 of the tube 24 is shaped to prevent air from being entrapped between the coupling of the inlet end 60 and the chamber outlet 42.

While in use, air bubbles 80 are generated as the droplets 46 strike the surface 82 of the pool 56. The bubble isolation device 22 prevents the air bubbles 80 from reaching the chamber outlet 42 so that the air bubbles 80 are able to return to the surface 82 of the pool 56 and be discharged. Also, the sponge 52 may be made of a molded open-cell foam that has a general pore size of about 10 to 20 microns with the preferred pore size being about 12 to 15 microns.

Also shown, the connection 90 between the tube 24 and the drip chamber 20 is a zero dead space connection. In other words, the inlet end 60 is shaped to be attached flush to the chamber outlet 42 so that air may not be entrapped at the connection 90 as the fluid 14 passes the connection 90 and purges the air from the tube 24.

Figure 3:
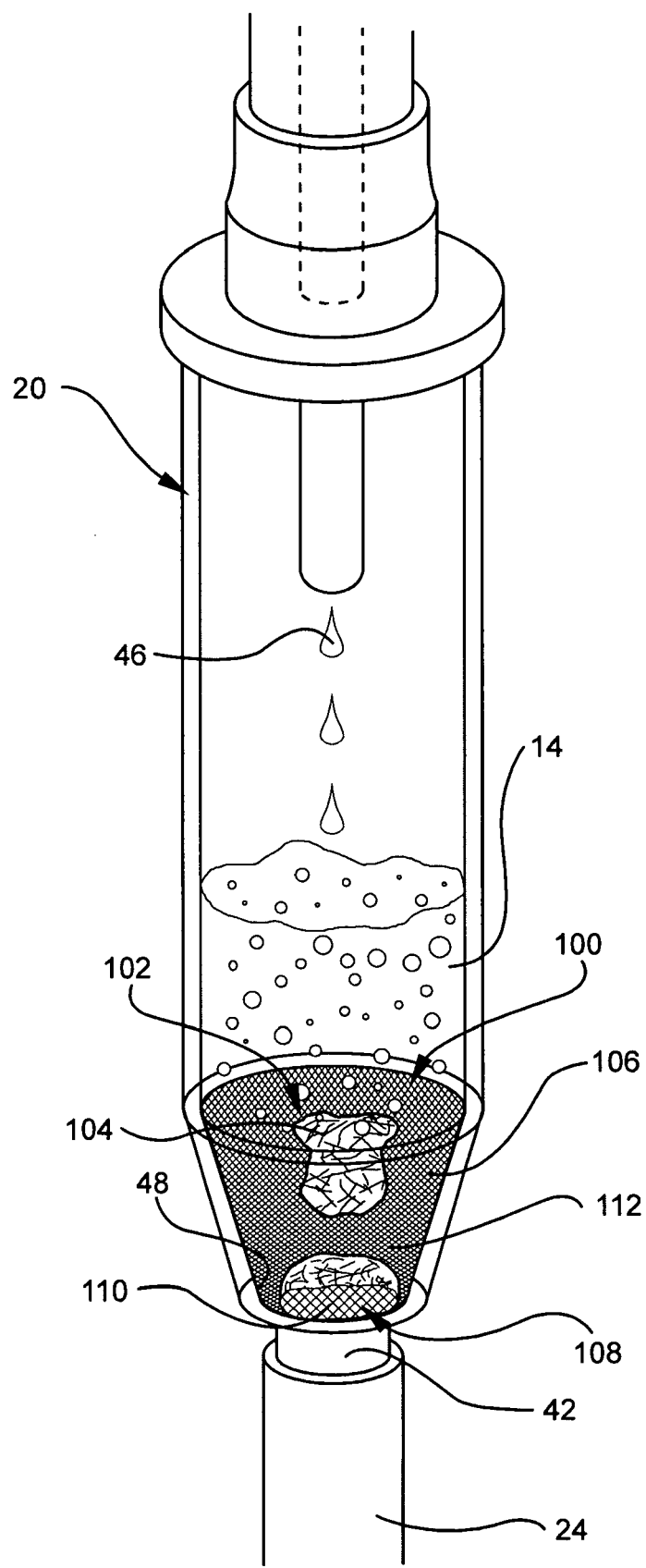
FIG. 3 is a perspective break-away view of an alternative bubble isolation device positioned within the drip chamber of FIG. 1.

FIG. 3 is a perspective break-away view and illustrates an alternative bubble isolation device 100 located within the drip chamber 20 of FIG. 1. As illustrated in FIG. 3, the bubble isolation device 100 comprises an absorbent structure 102 which includes a mat 104 of material covered by a woven material 106. The material of both the mat 104 and the woven material 106 may be hydrophilic, such as cotton. For example, the mat 104 may be a cotton ball and the woven material 106 may be gauze.

The fibers of the mat 104 may be sintered or adhered together to prevent material from the mat 104 from becoming separated from the mat 104 and entering the tube 24. The woven material 106 further helps to prevent material from entering the tube 24.

Additionally, the bubble isolation device 100 may include a particulate filter 108 positioned to prevent solid material from exiting the tube 24. The particulate filter 108 may be positioned in the drip chamber 20 or in the tube 24. As shown, the particulate filter 108 includes a screen 110 that may be positioned over the chamber outlet 42. The absorbent structure 102 is shaped to match the profile of the bottom surface 48 of the drip chamber 20 and is disposed to abut the bottom surface 48 around the particulate filter 108. Thus, the absorbent structure 102 covers the screen 110 of the particulate filter 108 and the chamber outlet 42.

The screen 110 and the absorbent structure 102 together form an active portion 112 of the bubble isolation device 100. Therefore, the active portion 112 of the bubble isolation device 100 completely covers the chamber outlet 42 so that air bubbles are not trapped under the bubble isolation device 100 or in the tube 24. In addition to the configuration described above and shown in FIG. 3, the particulate filter 108 may be used with any of the bubble isolation devices disclosed herein.

The bubble isolation device 100 functions similarly to the bubble isolation device 22 described above by absorbing the liquid 14 and then allowing the liquid 14 to enter the tube 24 once the bubble isolation device 100 has been saturated. The bubble isolation device 100 also acts to impede the flow rate of the liquid 14 from the drip chamber 20 into the tube 24.

Figure 4:
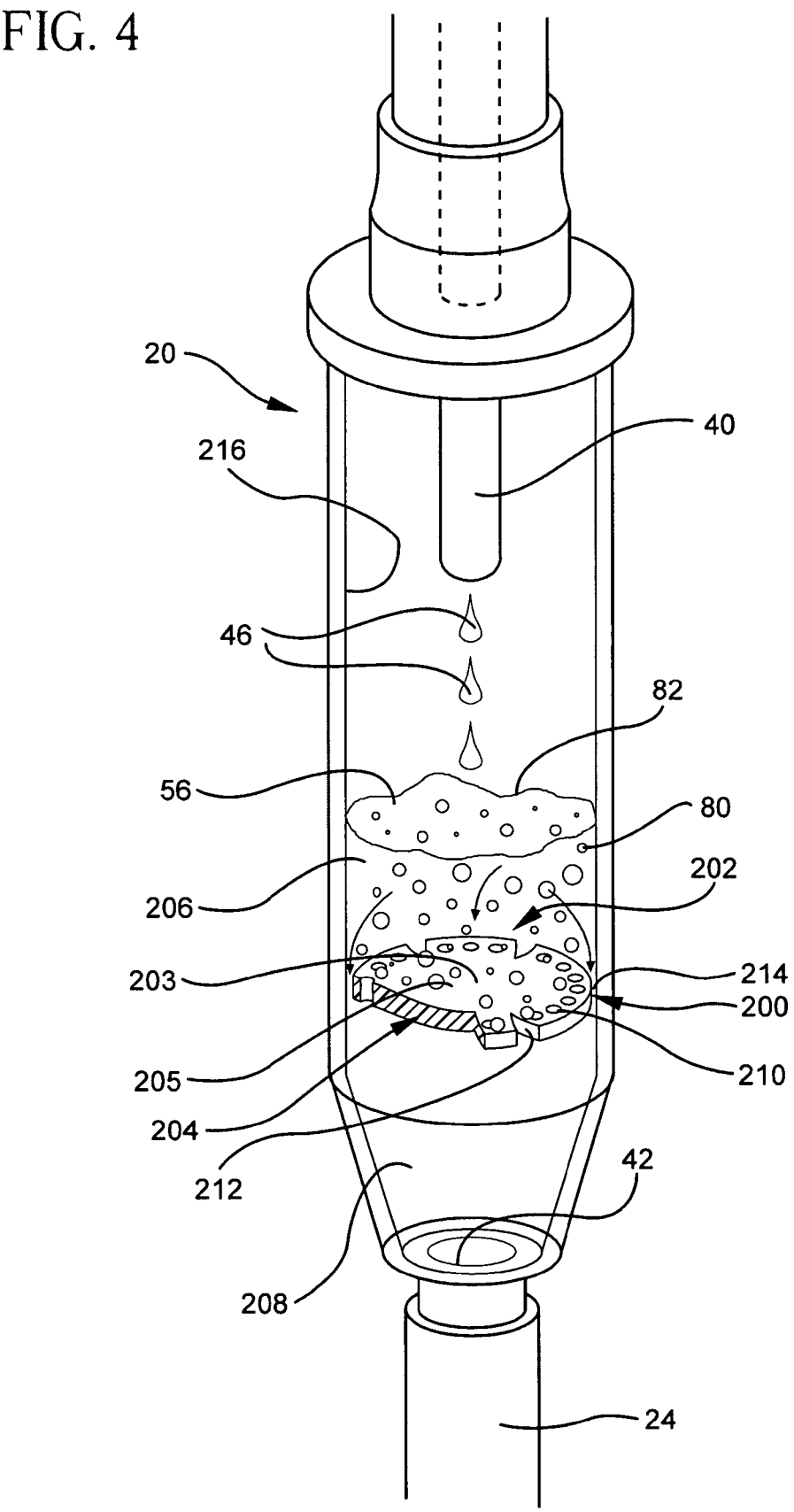
FIG. 4 is a perspective break-away view of another bubble isolation device disposed within the drip chamber of FIG. 1.

FIG. 4 is a perspective break-away view illustrating another bubble isolation device 200 positioned within the drip chamber 20 of FIG. 1. The bubble isolation device 200 prevents air bubbles 80 from exiting the chamber outlet 42. As shown, the bubble isolation device 200 includes a concave surface 202 positioned under the chamber inlet 40 so that the droplets 48 are directed toward the concave surface 202. In some configurations, the concave surface 202 may follow a parabolic curve or may have a set radius. Furthermore, the concave surface 202 may include a solid surface in the middle portion 203 of the concave surface 202 and edge ports 204 about the periphery 205 of the concave surface 202.

The bubble isolation device 200 is located within the drip chamber 20 to partition the drip chamber 20 into a bubble isolation chamber 206 and a calm fluid chamber 208. Once the surface 82 of the pool 56 extends above the concave surface 202 of the bubble isolation device 200, the concave surface 202 isolates the bubbles in the bubble isolation chamber 206. For example, as the droplet 46 strike the surface 82 of the pool 56, air bubbles 80 are generated and move downward toward the concave surface 202. The concave surface 202 redirects the force of the impacting droplets 46 and movement of the air bubbles 80 back towards the surface 82 and away from the point of impact by the droplets 46. Thus, the concave surface 202 acts to prevent the air bubbles 80 from being kept in the liquid 14 by the later impact of the droplets 46.

Proximate the periphery 205 of the concave surface 202, the liquid 14 calms and is able to flow through the edge ports 204 into the calm fluid chamber 208 bubble free. The edge ports 204 may be holes 210 extending through the bubble isolation device 200, cuts 212 positioned on the edges of the concave surface 202, or the edge ports 204 may be a gap 214 between the edge of the bubble isolation device 200 and a wall 216 of the drip chamber 20. The fluid 14 then moves from the calm fluid chamber 208 into the tube 24 through the chamber outlet 42.

The bubble isolation device 200 is generally able to handle much higher flow rates of fluid 14 than the bubble isolation devices 22 and 100 described above, because the flow of the liquid 14 does not have to pass through an absorbent structure or a filter. To position the concave surface 202 the bubble isolation device 200 may be adhered to the drip chamber 20, fastened in place using a mechanical fastener (not shown), or may be supported by support structure (not shown).

The bubble isolation device 200 may be made of metal, plastic, ceramic, or composite. For example, the bubble isolation device 200 may be made of an injection molded elastomer such as polypropylene. Additionally, the bubble isolation device 200 may be combined with any of the other bubble isolation devices disclosed herein. As shown, the bubble isolation device 200 may be a curved disc having concave surface 202 that is solid. The bubble isolation device 200 may be made by injection molding a plastic such as polyethylene. Alternatively, the concave surface 202 may be porous in configuration where the concave surface 202 is formed as part of an absorbent structure described above.

Figure 5:
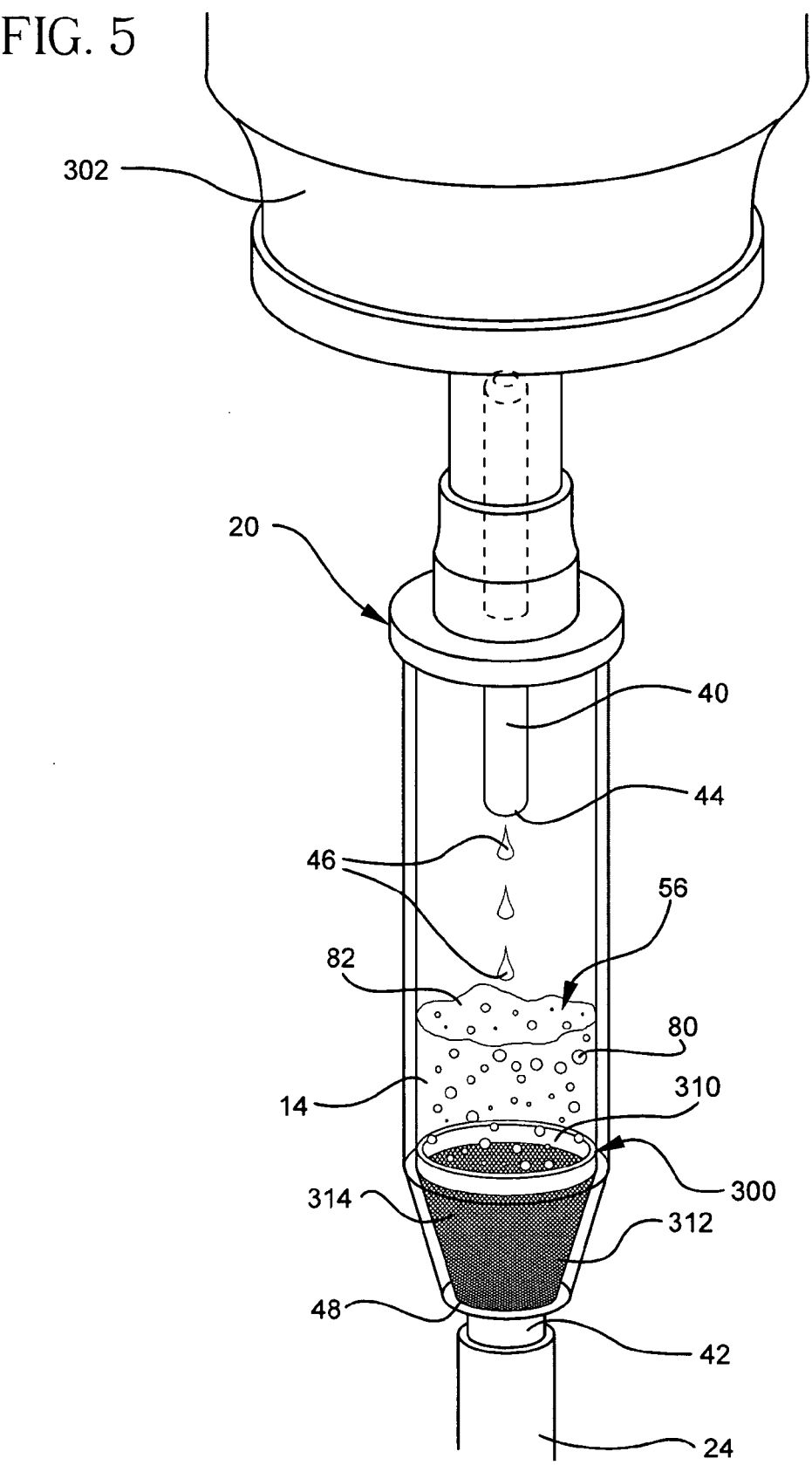
FIG. 5 is perspective view of an additional bubble isolation device disposed within the drip chamber of FIG. 1 coupled to an IV bottle.

FIG. 5 is perspective view of an additional bubble isolation device 300 disposed within the drip chamber 20 of the IV set 10 coupled to an IV bottle 302. As shown, the bubble isolation device 300 includes a frame 310 supporting an active portion 312 that includes a filter 314 which may be made of hydrophilic material. The filter 314 is shaped to match the profile of the bottom surface 48 and is positioned within the drip chamber 20 so that the filter 314 abuts the bottom surface 48 and covers the chamber outlet 42.

By disposing the active portion 312 to completely cover the chamber outlet 42, air is prevented from being trapped between the bubble isolation device 300 and the bottom surface 48 of the drip chamber 20. Additionally, the filter 314 may be sized so that the first droplet 46 of liquid 14 entirely wets the filter 314, which when wet prevents air from passing through the filter 314.

As liquid 14 collects in the pool 56 above the bubble isolation device 300, the air bubbles 80 are allowed to rise to the surface 82 of the pool 56. The air in the tube 24 is kept under the bubble isolation device 300 until the clamp 26 is released. Once the clamp 26 is opened, the liquid 14 is allowed to push the air in the tube 24 out of the end plug 30. As noted above, the end plug 30 restricts the flow of air out of the tube 24 so that the flow rate of liquid 14 out of the drip chamber 20 is retarded in order to prevent the formation of a "bubble ladder." A "bubble ladder" occurs when rate out of the drip chamber 20 is greater than the flow rate into the drip chamber 20 and the pool 56 is small enough that air is intermittently pulled through the bubble isolation device 300 and into the tube 24 so that air and liquid 14 form successive layers in the tube 24.

The bubble isolation devices 22, 100, 200, 300 disclosed above may be made of metal, plastic, ceramic, or a composite material. Additionally, some configurations of the bubble isolation devices 22, 100, 200, 300 may be made by machining processes, molding processes, and other manufacturing processes known by those of skill in the art.

A method of using an IV set according to the invention, such as the IV set 10 of FIG. 1, may include the steps of closing the clamp 26 and coupling the chamber inlet 40 of the drip chamber 20 to a source of the liquid 14, such as an IV bag 12, IV bottle 302, or other source of liquid known in the art. The drip chamber 20 may be squeezed to draw the fluid 14 into the drip chamber 20. Once the fluid 14 enters the drip chamber 20, it wets the bubble isolation device, such as 22, 100, 200, 300, with the liquid 14.

Once the drip chamber 20 is filled about ⅓ to about ½ full of liquid 14, the clamp 26 is opened to permit the liquid 14 to flow through the tube 24. The bubble isolation device 22, 100, 200, 300 is used to prevent air bubbles 80 from reaching the chamber outlet 42 and the end plug 30 is used to restrict the venting of air from the tube 24 as liquid 14 flows through the tube 24 so that the fluid flow through the tube 24 is generally laminar. The end plug 30 may also be used to prevent liquid from exiting the outlet end 62 of the tube 24 and to restrict the venting of air from the tube 24 as liquid 14 flows through the tube 24 so that the volume of fluid 14 flowing through the chamber inlet 40 is greater than or about equal to the liquid flow through the chamber outlet 42.

If the bubble isolation device 22, 100 is an absorbent structure 54, 102, the method may include the step of absorbing the liquid 14 in the absorbent structure 54, 102 so that liquid 14 does not pass the chamber outlet 42 until the absorbent structure 54, 102 is saturated. Additionally, a particulate filter 108 may be used to prevent material from the bubble isolation device 22, 100 from exiting the tube 24.

In other embodiments of the invention, the method may include using the bubble isolation device 200 to partition the drip chamber 20 into a bubble isolation chamber 206 and a calm fluid chamber 208 and using the concave surface 202 of the bubble isolation device 200 to retain the air bubbles 80 in the bubble isolation chamber 206. If the IV set 10 includes a zero dead space access port 28, the method also include the step of expelling all air from the zero dead space access port with the front of the liquid flowing through the tube.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. An IV set for use in the administration of liquid, the IV set comprising:
   a drip chamber comprising a chamber inlet and a chamber outlet;
   a bubble isolation device disposed within the drip chamber that substantially prevents air bubbles from exiting the chamber outlet wherein the combination of the bubble isolation device and drip chamber determine a first selected flow rate of fluid exiting the drip chamber;
   a tube having an inlet end and an outlet end, wherein the inlet end of the tube is coupled to the chamber outlet of the drip chamber; and
   an end plug comprising an air vent, having a porosity to limit the rate at which air is permitted to bypass the air vent, wherein the end plug is coupled to the outlet end of the tube, wherein the porosity of the air vent determines a second selected flow rate of fluid through the tube, wherein the first selected flow rate is greater than or about equal to the second selected flow rate such that flow of a liquid through the tube is generally laminar and such that when the liquid reaches the end plug, flow of the liquid through the tube is stopped.

2. The IV set of claim 1 wherein the velocity of the liquid flow through the tube is controlled such that a front of the liquid does not create bubbles.

3. The IV set of claim 1, wherein the bubble isolation device comprises a small pore filter that is shaped to match the profile of a bottom surface of the drip chamber and abuts the bottom surface of the drip chamber so that the small pore filter covers the chamber outlet.

4. The IV set of claim 1, wherein the bubble isolation device is an absorbent structure.

5. The IV set of claim 4, wherein the bubble isolation device comprises a sponge.

6. The IV set of claim 4, wherein the bubble isolation device comprises a woven material.

7. The IV set of claim 4, wherein the bubble isolation device comprises a mat.

8. The IV set of claim 1, further comprising a particulate filter which prevents material from the bubble isolation device from exiting the drip chamber and entering the tube.

9. The IV set of claim 1, wherein the bubble isolation device comprises a concave surface disposed within the drip chamber so that the liquid entering the drip chamber through the chamber inlet is directed toward the concave surface.

10. The IV set of claim 9, wherein the bubble isolation device partitions the drip chamber into a bubble isolation chamber and a calm fluid chamber.

11. The IV set of claim 9, wherein the concave surface follows a parabolic curve.

12. The IV set of claim 9, wherein the concave surface comprises edge ports.

13. The IV set of claim 9, wherein the concave surface comprises a solid middle portion.

14. The IV set of claim 1, wherein the tube comprises a zero dead space access port disposed between the inlet end and the outlet end.

15. The IV set of claim 1, wherein the end plug is removable.

16. An IV set for use in the administration of liquid, the IV set comprising:
   a drip chamber comprising a chamber inlet and a chamber outlet and comprising means for determining a first selected flow rate of fluid exiting the drip chamber;
   a means for preventing bubbles from exiting the chamber outlet;
   a tube having an inlet end and an outlet end, wherein the inlet end of the tube is coupled to the chamber outlet of the drip chamber; and
   means for venting air from the tube, wherein the venting means has a porosity to limit the rate at which air within the tube is permitted to bypass the venting means, the venting means further restricting the flow of air venting from the tube so that a liquid flows through the tube at a second selected flow rate during priming of the IV set, wherein the first selected flow rate is greater than or about equal to the second selected flow rate such that flow of the liquid through the tube is generally laminar and wherein when liquid reaches the outlet end of the tube, liquid flow through the tube stops.

17. The IV set of claim 16, wherein the velocity of the liquid flow through the tube is controlled such that a front of the liquid does not create bubbles within the tube.

18. The IV set of claim 16, wherein the preventing means comprises an active portion and is shaped to match the profile of a bottom surface of the drip chamber and abuts the bottom surface of the drip chamber so that only the active portion of the preventing means covers the chamber outlet.

19. The IV set of claim 16, further comprising a particulate filter which prevents material from the preventing means from exiting the drip chamber and entering the tube.

20. The IV set of claim 16, wherein the preventing means partitions the drip chamber into a bubble isolation chamber and a calm fluid chamber.

21. The IV set of claim 16, wherein the tube comprises a zero dead space access port disposed between the inlet end and the outlet end.

22. The IV set of claim 16, wherein the venting means is removable.

23. The IV set of claim 1 wherein the end plug is comprised of a hydrophobic material.

24. The IV set of claim 16, wherein the means for venting air from the tube comprises an end plug.

25. The IV set of claim 24, wherein the end plug comprises a hydrophobic material.

* * * * *